United States Patent [19]

Liotta et al.

[11] 4,079,468
[45] Mar. 21, 1978

[54] LOW PROFILE GLUTERALDEHYDE-FIXED PORCINE AORTIC PROSTHETIC DEVICE

[76] Inventors: Domingo Santo Liotta; Helio Mario Ferrari; Amadeo Joaquin Pisanu; Fidel Osvaldo Donato, all of St. 3 de Febrero 2025, Buenos Aires, Argentina

[21] Appl. No.: 735,576

[22] Filed: Oct. 26, 1976

[30] Foreign Application Priority Data

Jul. 28, 1976 Argentina .............................. 263750

[51] Int. Cl.² .............................................. A61F 1/22
[52] U.S. Cl. ....................................................... 3/1.5
[58] Field of Search ......................................... 3/1.5, 1

[56] References Cited

U.S. PATENT DOCUMENTS 3,983,581  10/1976  Angell et al. ............................. 3/1.5

OTHER PUBLICATIONS

"Surgery for Aortic Valve: Prosthesis and Heterograft" by M. J. Levy et al., *Surgery*, vol. 66, No. 2, pp. 313-318, Aug. 1969.

*Primary Examiner*—Ronald L. Frinks
*Attorney, Agent, or Firm*—Allison C. Collard

[57] ABSTRACT

A prosthetic device which includes a frame for mounting a gluteraldehyde-fixed porcine aortic valve and includes a sewing ring which surrounds the frame. The frame is provided with a proximal end and a distal end which extends beyond the ring, and the entire unit is covered with medical grade fabric.

12 Claims, 2 Drawing Figures

LOW PROFILE GLUTERALDEHYDE-FIXED PORCINE AORTIC PROSTHETIC DEVICE

BACKGROUND OF THE INVENTION

This invention relates to prosthetic devices, and in particular to low profile gluteraldehyde-fixed porcine aortic xenografts. More particularly, the invention tion is concerned with a low profile gluteraldehyde-fixed cardiac valve prepared from a porcine aortic valve.

Gluteraldehyde solution employed for fixation and preservation of the porcine and aortic valve is the same as the method of other tissue valves, for example, the Hancock type, the Carpentier type, etc. In addition, another feature in common with other tissue valves is the use of a frame in which the porcine aortic valve is mounted.

Anatomical studies demonstrate that in 90% of the specimens the depth of the sinuses of Valsalva were under 10 mm. Also, the aortic ridge is an important structure that joins the three commissures. The anatomic conclusions indicated the need and necessity of providing a low profile bio-prosthesis preserving the aortic ridge.

Protrusion of the frame into the LV (Left Ventricle) with risk of obstruction by the trabecular muscles, perforation of the posterior wall of LV and mainly various degrees of subaortic obstruction have been reported with the use of the current mounted aortic porcine xenograft. In addition, small ascending aorta will not freely accept a bulky prosthesis.

SUMMARY OF THE INVENTION

The complications with the low profile prosthetic heterograft are completely avoided.

Furthermore, the tissue valve will perform better and last longer because the normal functional architecture of the cusps are maintained.

The improved cardiac valve development was originated from a fundamental anatomic study, focusing on the size and dimension of 200 porcine aortic valves. The majority of the specimens examined revealed that the distance between the aortic ridge is under 11 mm, measured at the lower point in the sinus of Valsalva. These studies demonstrated the need for a low profile cardiac valve, preserving the anatomic relations of the porcine aortic valve. The observations were made before dissection and separation of the aortic valve from the surrounding anatomic structures in the heart.

The cardiac valve according to the invention has three distinct advantages over the other tissue valves.

1. It eliminates the intraventricular or the intra-aortic struts.
2. When implanted in the atrioventricular position, most of the body of the bio-prosthesis (10 mm height in the largest valve) remains in the atrium's cavity.
3. The aortic ridge and partially the sinuses of Valsalva are preserved.

A major source of complications and death shortly after valve replacement with a tissue valve is due to the inadequate space in the cardiac ventricle or in the ascending aorta to accommodate the valve readily, and to too small a ventricular cavity or aortic root to freely accept the bio-prosthesis. Consequently, the removal of the intraventricular and most of the intra-aortic portion of the bio-prosthesis prevents valve dysfunction produced by tissue valve disproportion.

In addition, obstruction of the outflow tract of the ventricle and impingement of the valve's frame on the intraventricular septum or on the left ventricular wall are definitively suppressed. Prosthetic dysfunction by prosthetic disproportion may also be served after valve replacement with a mechanical prosthesis, such as caged-ball and caged-disc prosthesis.

After implantation in the mitral annulus, most of the body of the new bio-prosthesis remains in the atrium's cavity. For example, 10 mm out of the 14 mm total height of the largest diameter valve, the No. 32, projects into the atrium. Bio-prosthesis with smaller diameters have proportionally smaller height dimensions. For example, the number 22, employed for aortic valve replacement, has only a 10 mm height.

Another important feature of this bio-prosthesis is the preservation of the aortic ridge. The aortic ridge is an anatomic formation, well observed in the lumen of the ascending aorta, separating the sinuses of Valsalva from the ascending aorta. It joins the three commissures or junctions of the aortic valve.

Histological observations of the commissures and the aortic ridge indicate the importance of these anatomic structures. In a semilunar valve leaflet, the dense middle layer becomes somewhat thickened along a line close to and parallel with its free margin. At the apex of each leaflet, this thickened line is accentuated to form the Arancio's module. At the commissures this thickened line of each leaflet is closely packed, and forms an interlacing network with the connective tissue of the adjacent leaflet. This dense fibro-elastic connective tissue of each commissure becomes continuous with the connective tissue of the aortic ridge.

The preserved aortic ridge avoids overmotion of the leaflets during the opening phase of the valve. It softens the commissures' stress during closures. In other words, it is believed that the valve will perform better and will last longer because the normal functional architectures of the cusps is maintained.

The removal of the aortic ridge weakens the anatomic structures of the valve. Therefore, in order to prevent a valve's failure to operate, the commissures must necessarily be stretch-out and mounted into a frame with long struts. This is the result of other tissue valves.

The porcine aortic valve dissected from the surrounding heart's tissue is fixed and preserved in gluteraldehyde solution. When the valve is submerged in gluteraldehyde solution, the aortic ridge must be slightly dilated, with a special designed instrument, to prevent excessive contraction of the aortic ridge.

Accordingly, it was necessary to provide a low profile frame for mounting the gluteraldehyde-fixed porcine aortic valve.

INTRODUCTION TO THE DRAWING (ONE EMBODIMENT)

DESCRIPTION OF THE PREFERRED EMBODIMENT

Figure 1:
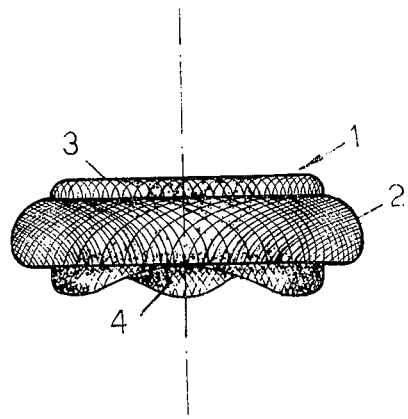
FIG. 1 is a side perspective view of the low profile implantable prosthetic device in accordance with the invention.
Figure 2:
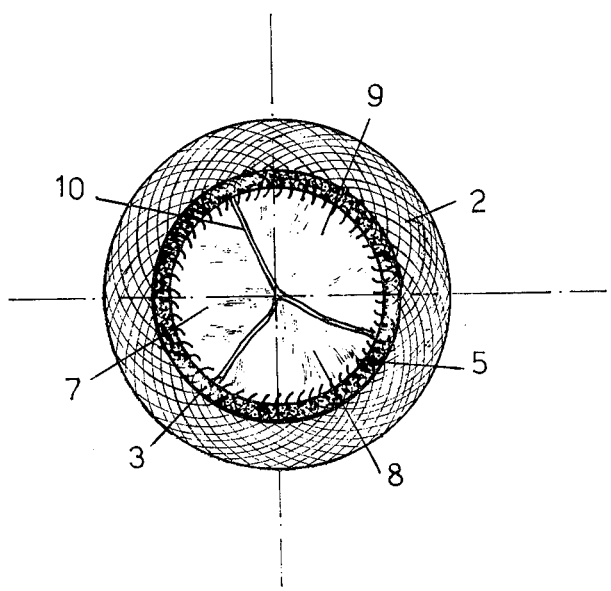
FIG. 2 is a front view of the prosthetic device of FIG. 1.

Referring to the drawing, the prosthetic device includes a frame 1 having a cylindrical shape. The frame has a solid and slightly flexible support. However, flexibility of the frame is not indispensible. The frame's support is fabricated from a medical grade plastic material or equivalent. The frame is covered with a medical grade fabric that could be high porosity Dacron material, or equivalent.

The frame is surrounded by an extension in the form of a sewing ring 2 which is to be used for valve implantation. The bio-prosthesis used for human aortic valve replacement has a small and flat sewing ring. The illustrated sewing ring 2 is for a mitral bio-prosthesis.

The proximal end 3 of the cylindrical frame is thin and includes a non-scalloped flat rim 11 with rounded edges 12, and the distal end 4 has a wavy or scalloped shape. Both ends of the cylindrical frame are covered with fabric material to permit the suturing of the aortic ring at the proximal end, and the aortic ridge at the distal end of the three porcine leaflets or cusps 7, 8, and 9, which are fixed together at their respective commissures or junctions 10. Proximal end 3 extends beyond ring 2 in one direction, and distal end 4 extends beyond ring 2 in the opposite direction.

The bio-prosthetic device of low profile prepared from the procine aortic valve permits the tissue valve to be mounted in a low profile cylindrical frame covered with the fabric material which permits fixation when used in mitral or aortic valve replacement.

The total height of the bio-prosthetic device is approximately half or less than the dimensions of the diameter of the mounted bio-prosthesis. For example, the total height of 14 mm corresponds to the largest tissue valve in the mitral series which is the number 32. Distal end 4 of the frame has the wavy or scalloped shape, and the distal end of the mounted bio-prosthetic device also has a scalloped or wavy shape.

286 Aortic porcine fresh specimens before dissection of the valve from the surrounding tissue were studied. In addition, 30 dissected and gluteraldehyde treated porcine aortic valves were examined. The low profile frame was provided for MVR with a total height of 11-14 mm. For AVR the total height is 7-10 mm.

A hydrodynamic evaluation of the low profile valve according to the invention was done. Pressure difference across the valve, regurgitation with increasing pressures up to 500 mm Hg, closing delay and the prolonged high speed motion of the aortic cusps were studied.

Eight aortic valves numbered 20-28 mm and four mitral 26-28 mm were prepared. Ten millimeters of the body of the mitral bio-prosthesis remains in the atrium's cavity. The hydrodynamic evaluation demonstrated an absent or very low pressure gradient (15 mm Hg - 15 liters/min.). Regurgitation starts with a closing pressure exceeding 500 mm Hg. The accelerated life testing indicated a permanent durability of the tissue valves.

While there has been shown what is considered to be a preferred embodiment of the invention, it will be obvious that various changes and modifications may be made therein without departing from the spirit and scope of the invention.

What is clamed is:

1. A stent for a gluteraldehyde-fixed porcine heart valve prosthesis comprising
a hollow, substantially cylindrical frame for mounting a gluteraldehyde-fixed porcine heart valve, said frame having a distal and proximal end, the distance between which about the entire circumference of said frame is between 7 and 14 millimeters; and
medical grade fabric covering the external and internal surfaces of the frame.

2. The stent according to claim 1 wherein said distance between said proximal and distal ends of said frame is between 7 and 11 millimeters to permit mounting of a porcine mitral valve.

3. The stent according to claim 1 wherein said distance between said proximal and distal ends of said frame is between 11 and 14 millimeters to permit mounting of a porcine aortic valve.

4. The stent according to claim 1 wherein said distal end has a scalloped edge.

5. The stent according to claim 1 wherein said proximal end has a flat circular rim with a rounded edge.

6. The stent according to claim 1 additionally including a sewing ring mounted on and surrounding said frame to permit suturing of said stent to a patient's intracardiac structures, said fabric material covering said ring and said frame.

7. The stent according to claim 6 wherein said sewing ring is disposed closely adjacent to said distal end of said stent.

8. A gluteraldehyde-fixed porcine heart valve prosthesis comprising:
a stent including a hollow, substantially cylindrical frame for mounting a gluteraldehyde-fixed porcine heart valve, said frame having a distal and proximal end, the distance between which about the entire circumference of said frame is between 7 and 14 millimeters;
medical grade fabric covering the external and internal surfaces of the frame; and
a gluteraldehyde-fixed porcine heart valve sutured to said stent.

9. The prosthesis according to claim 8 wherein said distance between said proximal and distal ends of said frame is between 11 and 14 millimeters to permit mounting of a porcine aortic valve.

10. The prosthesis according to claim 8 wherein said distal end has a scalloped edge.

11. The prosthesis according to claim 8 wherein said distance between said proximal and distal ends of said frame is between 7 and 11 millimeters to permit mounting of a porcine mitral valve.

12. The prosthesis according to claim 8 wherein said porcine valve has an aortic ring which is sutured to said proximal end by means of said fabric material and an aortic ridge which is sutured to said distal end by means of said fabric material.

* * * * *